(12) United States Patent
DuBois et al.

(10) Patent No.: US 7,341,153 B2
(45) Date of Patent: Mar. 11, 2008

(54) VIEWABLE SPECIMEN PACKAGING SYSTEM AND METHOD

(75) Inventors: Dwight B. DuBois, Austin, TX (US); Timothy W. Murray, Cumming, GA (US)

(73) Assignee: Cenetron Diagnostics, Ltd.

( * ) Notice: Subject to any disclaimer, the term of this patent is extended or adjusted under 35 U.S.C. 154(b) by 485 days.

(21) Appl. No.: 10/614,305

(22) Filed: Jul. 3, 2003

(65) Prior Publication Data

US 2005/0000841 A1    Jan. 6, 2005

(51) Int. Cl.
B65D 85/42 (2006.01)
B65D 25/54 (2006.01)

(52) U.S. Cl. ............... 206/769; 206/45.25; 206/45.29; 206/769; 229/120.02; 229/162.6

(58) Field of Classification Search ............. 206/45.21, 206/45.23, 45.25, 45.28, 769, 776, 45.29, 206/120.02; 229/120.02, 120.07, 120.32, 229/162.6, 909
See application file for complete search history.

(56) References Cited

U.S. PATENT DOCUMENTS

| | | | | | |
|---|---|---|---|---|---|
| 1,674,209 | A | * | 6/1928 | Lord | 206/589 |
| 1,961,293 | A | * | 6/1934 | Hassell | 206/521.6 |
| 1,961,294 | A | * | 6/1934 | Hassell | 206/521.6 |
| 2,192,307 | A | * | 3/1940 | Green | 206/521.1 |
| 2,665,026 | A | * | 1/1954 | Katzman | 217/22 |
| 2,758,774 | A | * | 8/1956 | Grunert et al. | 229/117.07 |
| 2,840,228 | A | * | 6/1958 | Takacs | 206/769 |
| 2,919,844 | A | * | 1/1960 | Anderson, Jr. | 229/120.011 |
| 3,045,888 | A | * | 7/1962 | Forrer | 229/125.19 |
| 3,108,685 | A | * | 10/1963 | De Vines | 206/321 |
| 3,185,296 | A | * | 5/1965 | Schlage | 206/776 |
| 3,233,726 | A | * | 2/1966 | George | 229/120.15 |
| 3,297,191 | A | * | 1/1967 | Eastman | 220/512 |
| 3,595,382 | A | * | 7/1971 | Hofer | 206/215 |
| 3,642,125 | A | * | 2/1972 | Johnson | 206/225 |
| 4,892,195 | A | * | 1/1990 | Slavin et al. | 206/473 |
| 4,915,224 | A | * | 4/1990 | Wulf et al. | 206/423 |
| 5,624,032 | A | * | 4/1997 | Yucknut et al. | 206/433 |
| 5,934,551 | A | * | 8/1999 | Kaufman | 229/162.6 |
| 6,871,778 | B2 | * | 3/2005 | Petrelli et al. | 229/120.18 |

* cited by examiner

*Primary Examiner*—John A. Ricci
(74) *Attorney, Agent, or Firm*—The Law Firm of H. Dale Langley, Jr., P.C.

(57) ABSTRACT

A specimen package includes a top, a first side, connected to the top, a bottom, connected to the first side, and a second side, connected to the bottom. The package also includes therein an internal separator. The internal separator forms a first compartment and a second compartment within the package. The top includes a window for viewing the first compartment. The bottom includes a second window for viewing the second compartment. The top, the first side, the bottom, the second side, and the internal separator can all be formed by folding a shaped planar sheet. The first compartment can contain a specimen, placeable within the first compartment. The second compartment can contain a label, placeable within the second compartment. The specimen is viewable through the first window, and the label is viewable through the second window.

2 Claims, 5 Drawing Sheets

VIEWABLE SPECIMEN PACKAGING SYSTEM AND METHOD

BACKGROUND OF THE INVENTION

The present invention generally relates to medically and biologically-related devices and, more particularly, to clinical and laboratory specimen containers and packagings with viewing windows.

Typically, packages or containers for containing laboratory specimens and the like are enclosures formed of opaque materials, such as cardboard, paper, fiberboard, or similar materials. Once such a package is filled with contents, the package is closed. The contents are not viewable from outside the package. Therefore, mistakes can be made in filling the package and labeling or identifying the package contents. After the package is closed, it must either be opened (often requiring break of a seal or other affixer) or reliance placed on accuracy of the filling.

With certain packaged materials, in particular, such as laboratory specimens, clinical collection kits, and other matters, it would be advantageous to be able to confirm package contents. Furthermore, it would be advantageous to be able to confirm that documentation for the package, and included within the package, corresponds to the particular package contents.

Thus, it would be a significant improvement in the art and technology to provide improved containers and packages. Additionally, it would be such an improvement to provide features of such containers and packages for viewing and ascertainment of contents. The present invention provides numerous advantages and improvements, including, for example, automation of certain cleaning processes, reduced manpower requirements in such processes, and additional capabilities and modes for performing the processes.

SUMMARY OF THE INVENTION

An embodiment of the invention is a container. The container includes a first internal compartment, a second internal compartment, a first window for viewing the first internal compartment, and a second window for viewing the second internal compartment.

Another embodiment of the invention is a collection package. The package includes a top, a first side, connected to the top, a bottom, connected to the first side, a second side, connected to the bottom, and an internal separator.

Yet another embodiment of the invention is a method of forming a container. The method includes folding a sheet to form a first side, folding the sheet to form a top, folding the sheet to form a second side, folding the sheet to form a bottom, and folding the sheet to form an internal separator.

A further embodiment of the invention is a method of containing a specimen. The method includes forming a container having a first internal compartment and a second internal compartment, forming a first window in the container for viewing the first internal compartment, and forming a second window in the container for viewing the second internal compartment.

Another embodiment of the invention is a system. The system includes a fillable container and a separator contained internally within the fillable container. A first window and a second window of the fillable container allow viewing of respective contents of the fillable container.

BRIEF DESCRIPTION OF THE DRAWINGS

The present invention is illustrated by way of example and not limitation in the accompanying figures, in which like references indicate similar elements, and in which.

DETAILED DESCRIPTION

Figure 1:
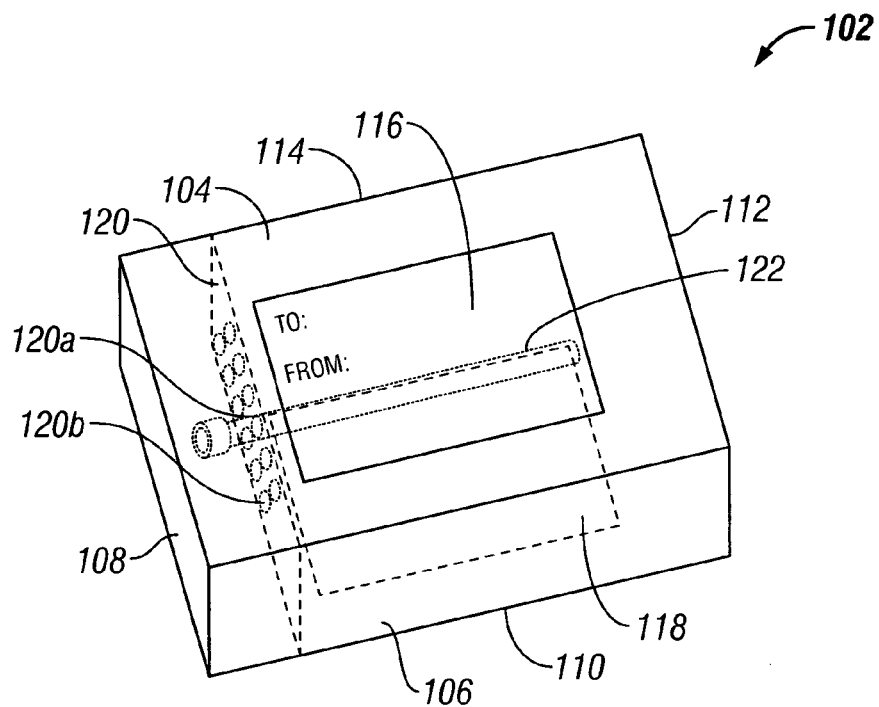
FIG. 1 illustrates a perspective view, shown with top-side up, of a system for packaging, according to certain embodiments of the invention.

Referring to FIG. 1, a container 100 is cubical or rectangular-boxed in shape. The container 100 has a top side 104, a top end 108 and a left side 106. The container also has a bottom side 110, a bottom end 112, and a right side 114, although these are not visible or shown in FIG. 1. The top side 104 and the bottom side 110, the top end 108 and the bottom end 112, and the left side 106 and the right side 114, each respectively corresponds and respectively has the same size and shape. The container 100 also includes a top window 116 and a bottom window 118, formed respectively as openings in the top side 104 and the bottom side 110. [As further described herein, the windows 116, 118 permit "viewing" of contents. The term "viewing" and the like, as used herein, is intended to and should be construed and interpreted in the broadest possible manner to include all possible means of ascertaining or determining contents, e.g., including, but not limited to, such means as bar code scanning, light detection or measurement, illumination, microscope and spectrometer detection, x-ray, other scanning or ascertainment, and any other non-invasive means of determining or detecting contents. Viewing also includes, however, more traditional and simple means such as human eyesight investigation and the like.]

The container 100 is formed of a cardboard, paper, fiber or other material. Each of the top window 116 and the bottom window 118 is formed of a cellophane, plastic, or other transparent- or translucent-like material. As hereinafter described in detail, the container 100 can comprise a single or multiple pieces forming the various top, bottom, sides and ends. The container 100 can also include folded or otherwise formed portions, from single pieces or multiple pieces.

Additionally, the windows can be formed integral with the container 100 or can be added or missing in the container 100, depending on the application and desires.

The container 100 internally includes a vial tray 120. The vial tray 120 is suspended, lodged, fixed or otherwise disposed inside the top, bottom, sides and ends of the container 100. The vial tray 120 is, for example and as shown in FIG. 1, located towards the top end 108 of the container 100. The vial tray 120 is formed with one or more holes 120a,b (e.g., a total of twelve holes are shown for exemplary purposes in the Figures). The hole 120a is sufficient to accept and retain a specimen vial or other feature to be contained within the container 100. In a particular use, although not the only or limited use, the vial tray 120 serves to support a laboratory specimen test tube or other element, such as, for example, a vial 122. Several vials or other features can be placed and supported in the vial tray 120, where the vial tray 120 and its holes 120a,b are appropriately designed or formed, according to the desired application and use of the container 100. In this manner, the container 100 serves as a package or enclosure for maintaining the features or elements within the container 100.

The bottom side 110 of the container 100, particularly the bottom window 118, allows viewing of the features or elements, such as the vial 122, contained in the container 100. The top side 104 of the container 100 can also allow viewing of features or elements contained in the container 100. However, as hereafter more fully detailed, the container 100 can also include a slip ledge (not shown in FIG. 1, but later shown in detail in certain Figures), wherein the slip ledge can serve as a second internal repository of the container 100, such as for retaining an invoice, packing slip, contents list, bar code emblem, or other similar planar or other shape piece. In the exemplary illustration of FIG. 1, a mailing label is viewable through the top window 116. The mailing label in this example is retained within the second internal repository formed by the slip ledge of the container 100.

Figure 2:
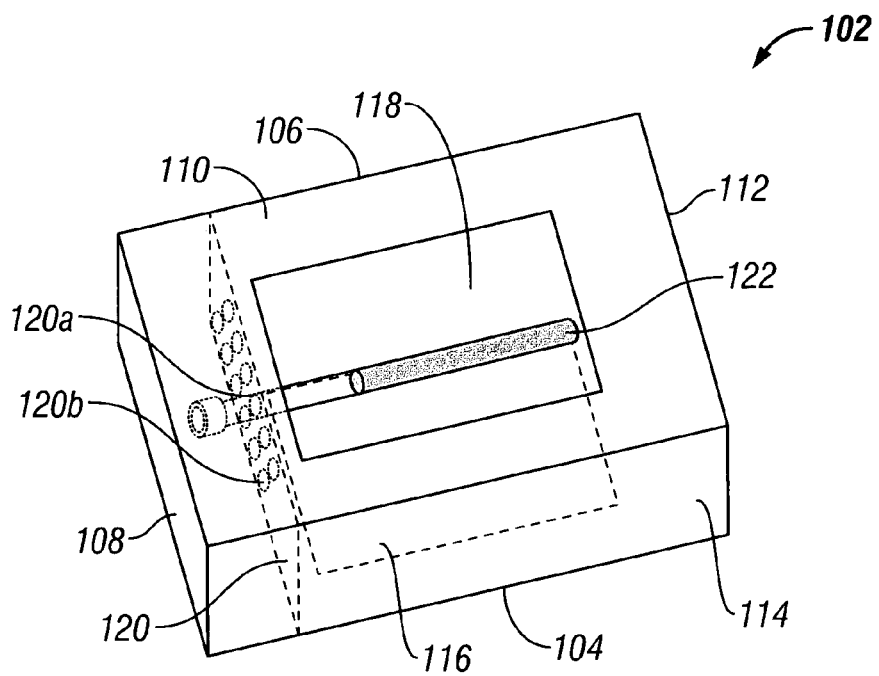
FIG. 2 illustrates a perspective view, shown with bottom-side up, of the system for packaging of FIG. 1, according to certain embodiments of the invention.

Referring to FIG. 2, the container 100 of FIG. 1 is oriented so that the bottom side 110 is upward in the view. The container 100 includes all of the elements and features described with respect to FIG. 1. In FIG. 2, however, the bottom window 118 formed of the bottom side 110 of the container 100 allows viewing of contents of the container 100. As an example, the contents of the container 100 are the vial 122 protruding into and through the vial tray 120. The bottom window 118 allows viewing of the vial 122 and any contents therethrough. In this manner, the vial 122 or other contents (e.g., identification, bar codes, or other matters) of the container 100 can be viewed and assessed for accuracy, proper inclusion, location or other aspects or characteristics. For example, the viewing can allow quality control of the contents of the container 100 after it is sealed.

Figure 3:
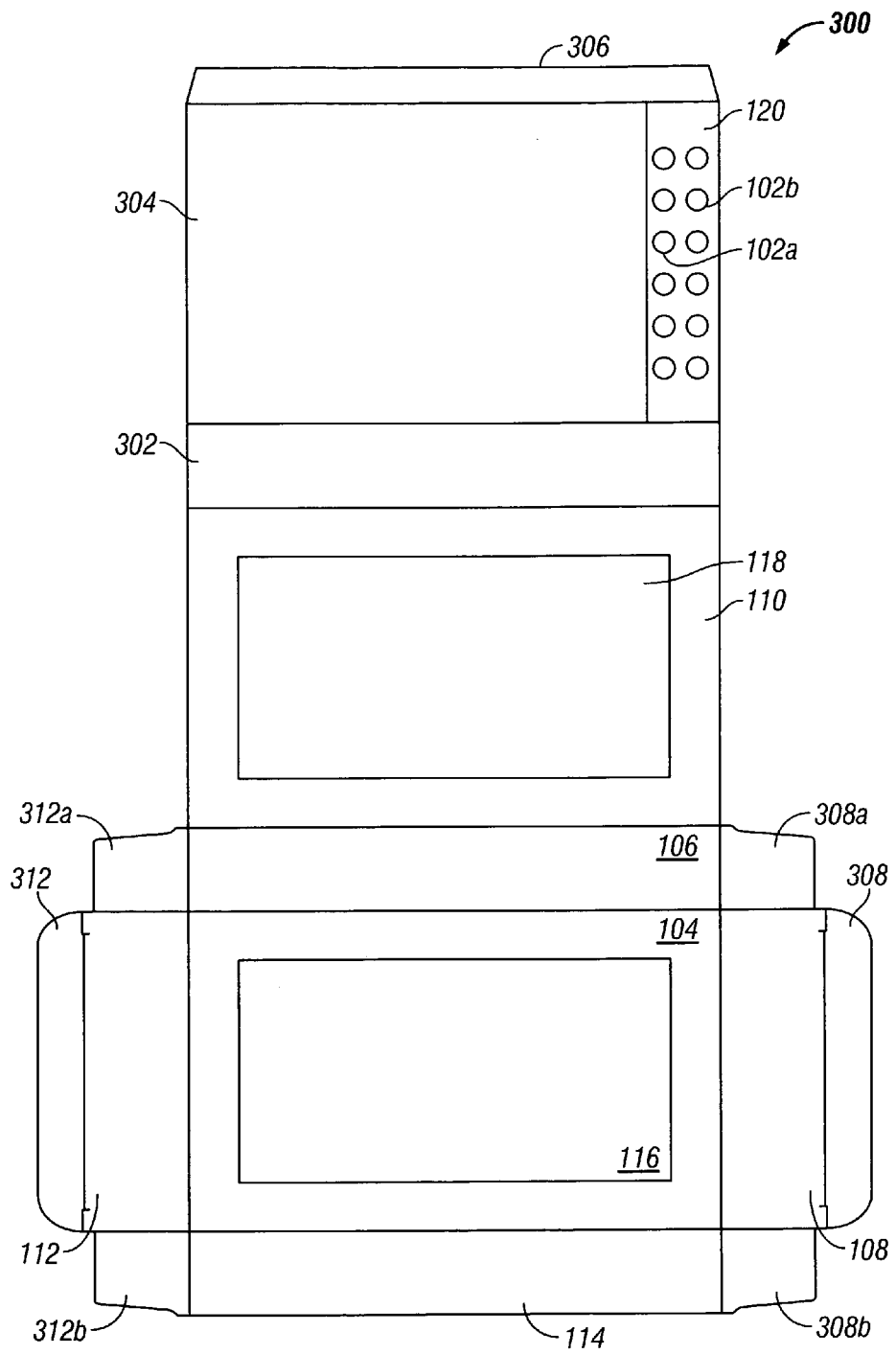
FIG. 3 illustrates an unfolded, flat and laid-out, view of the system for packaging of FIGS. 1 and 2, according to certain embodiments of the invention.

Referring to FIG. 3, a flat sheet 300, for forming the container 100 from a single piece, comprises all of the features shown in FIGS. 1 and 2. Particularly, the flat sheet 300 is formed by shaping and cutting (and subsequent folding) to include the left side 114, the top side 104 with the top window 116, the right side 106, the bottom side 110 with the bottom window 118, and the top end 108 and the bottom end 112. Additionally, the flat sheet includes an internal side 302 and a slip ledge 304 (as previously mentioned). A portion of the slip ledge 304 (oriented to the right side in FIG. 3) is shaped and foldable to form the vial tray 120. As previously described, the vial tray 120 is formed with holes 100a,b or other insertion openings for contents of the container 100.

In addition to the foregoing pieces, the flat sheet 300 is shaped and cut (for subsequent folding) forming a ledge lip 306 adjacent the slip ledge 304, a top lip 308 adjacent the top end 108, a bottom lip 312 adjacent the bottom end 112, and respective top end folds 308a,b and bottom end folds 312a,b. As desired or required, the end folds 308a,b and 312a,b are separated from the respective top end 108 and bottom end 112, to enable folding and enclosure as hereafter further detailed. Moreover, the vial tray 120, as desired or required, is separated from the ledge lip 306 and from the internal side 302, also to enable folding and enclosure, as well as desired positioning, internally for the container 100.

Figure 4:
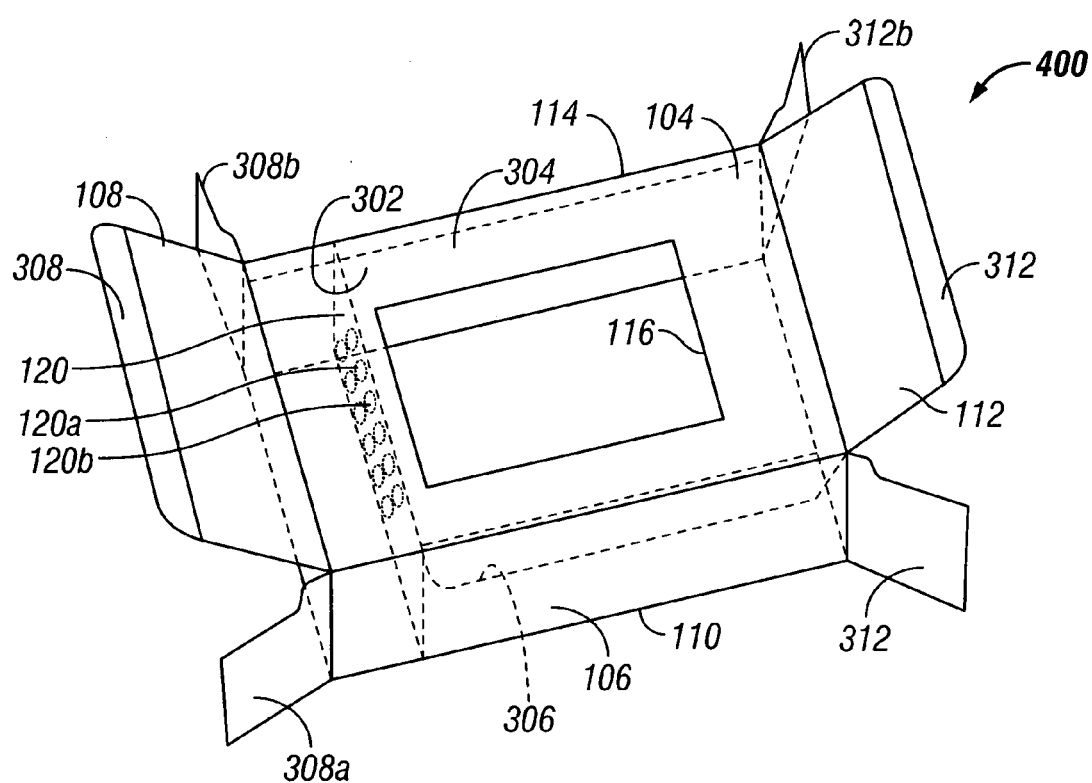
FIG. 4 illustrates a perspective view, shown with top-side up, of the system for packaging of FIGS. 1–3, having open and unclosed ends, according to certain embodiments of the invention.

Referring to FIG. 4, the flat sheet 300 of FIG. 3 is folded to form the container 400 (substantially like the container 100 of FIGS. 1 and 2). The ledge lip 306 is folded (lengthwise from end to end) to a right angle with the slip ledge 304. The vial tray 120 is also folded (widthwise from side to side) to a right angle with the slip ledge 304. The vial tray 120 separates from the ledge lip 306 and the internal side 302 on such folding.

The slip ledge is folded (lengthwise from end to end) to a right angle with bottom side 110. The bottom side 110 is folded (lengthwise from end to end) to a right angle with the right side 106. The right side 106 is folded (lengthwise from end to end) to a right angle with the top side 108. The top side 106 is folded (also lengthwise from end to end) to form a right angle with the left side 114.

The respective end folds 108a,b are folded with respect to the right side 106 and left side 114, respectively. The end folds 108a,b separate from the top end 108 on such folding. Similarly, the respective end folds 312a,b are folded with respect to the right side 106a and left side 114, respectively. The end folds 312a,b separate from the bottom end 112 on such folding. The top lip 308 and the bottom lip 312 are folded at right angles with respect to the top end 106 and the bottom end 312, respectively.

In relation to the view of the sheet 300 of FIG. 3, all folds previously described are made into the page of the Figure. In three-dimensional orientation, all folds of the sheet 300 are made inward towards the inside of the container 400 (i.e., also, the container 100 when formed as shown in FIGS. 1 and 2).

Internally to the container 400, the ledge lip 306 can affix to an internal side of the right side 106. The ledge lip 306 is affixed by glue, staple, or other fixed or removable securement means. As the ledge lip 306 is so affixed, the slip ledge 302 is planarly located some distance from the top side 104. This forms an individual compartment within the container 400, suitable for accepting a feature or device, such as, for example, a slip of paper that serves as a mailing label, invoice, bar code, emblem, identification or other. The top window 116 allows viewing of any feature or device so disposed in the individual compartment of the container 400. Another individual compartment within the container 400 is also formed via the slip ledge 302, between the slip ledge 302 and the bottom side 110. This other compartment within the container 400, is suitable for accepting a separate feature or element, such as, for example, a vial or other specimen (together with any appropriate identifying information) positioned through the vial tray 120 within the container 400.

The left side 114 of the container 400 affixes to the internal side 302, where the sides touch when the container 400 is folded in the manner shown and described. The left side 114 is affixed to the internal side 302 by glue, staple, or other fixed or removable securement means. This forms the container 400 with open ends (top end 108 and bottom end 112, respectively) as shown in FIG. 4.

Figure 5:
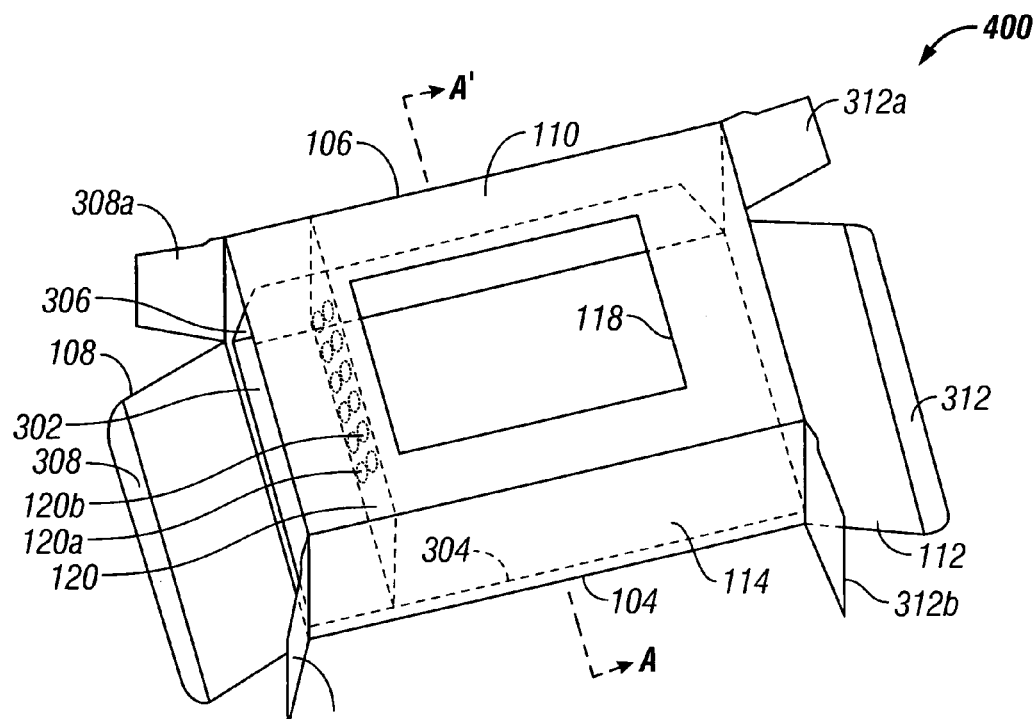
FIG. 5 illustrates a perspective view, shown with bottom-side up, of the system for packaging of FIGS. 1–3, having, opened and unclosed, a top end and a bottom end, according to certain embodiments of the invention.

Referring to FIG. 5, the container 400 of FIG. 4 is shown oriented with the bottom side 110 up in the view. (In effect, the container 400 of FIG. 4 is flipped over 180° along the length.) In the orientation of the container 400 shown in FIG. 5, the slip ledge 302 is seen situated within the tops and sides of the container 400, planarly a small distance from the top side 104. In phantom, the vial tray 120 is disposed widthwise across the inside of the container 400. The ledge lip 306 is fixed internally to the right side 306. The internal side 304 is fixes internally to the left side 114. The ends of the container 400 are open in FIG. 5, showing the respective ends (e.g., respectively, comprising the top end 108 and top lip 308, together with end flaps 308a,b, and comprising the bottom end 112 and bottom lip 312, together with end flaps 312a,b.

Figure 6:
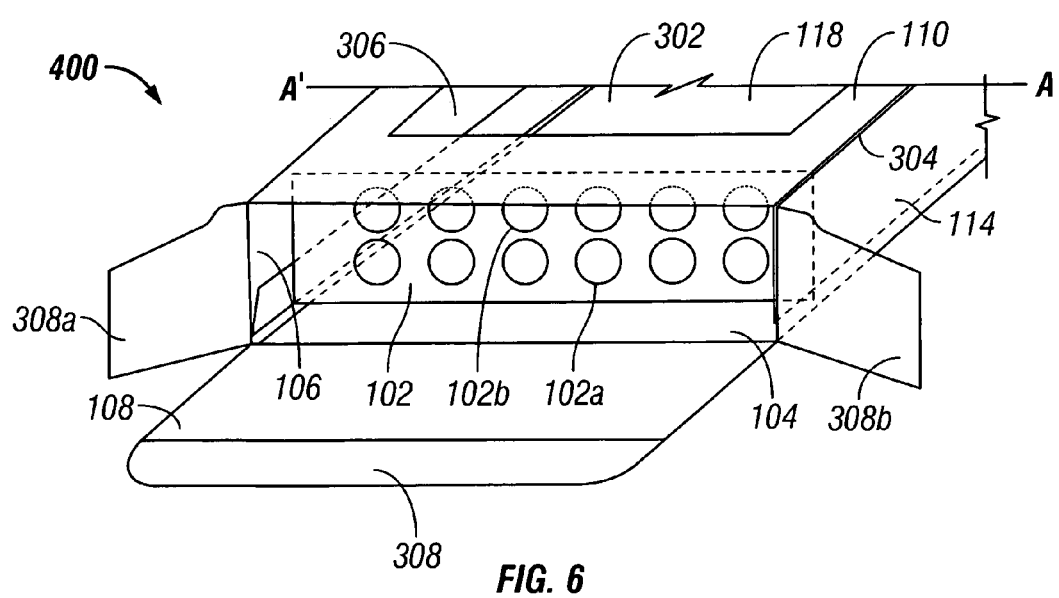
FIG. 6 illustrates a partial perspective view into the top end, open and unclosed, of the system for packaging, including (partially in phantom) a vial tray of the system, according to certain embodiments of the invention.

Referring to FIG. 6, the container 400 is shown from the open top thereof, as a section taken along lines A–A' of FIG. 5. In the orientation of FIG. 6, the left side 114 is shown affixed with the internal side 304. The right side 106 is shown affixed with the ledge lip 306. A planarly configured slip space is formed between the slip ledge 302 (as viewable through the bottom window 116 of the bottom side 110) and the top side 104, internally in the container 400. The top end 108, with top lip 308, and the end flaps 308a, 308b, are opened, to allow insertion of matters within the container (e.g., either into the slip space between the slip ledge 302 and the top side 104, or into the insides of the container 400 through the vial tray 120 and within the confines of the bottom side 110 and slip ledge 302. The vial tray 120, together with its holes 100a,b, is positioned within the open end of the container 400 and across the cross section.

Figure 7:
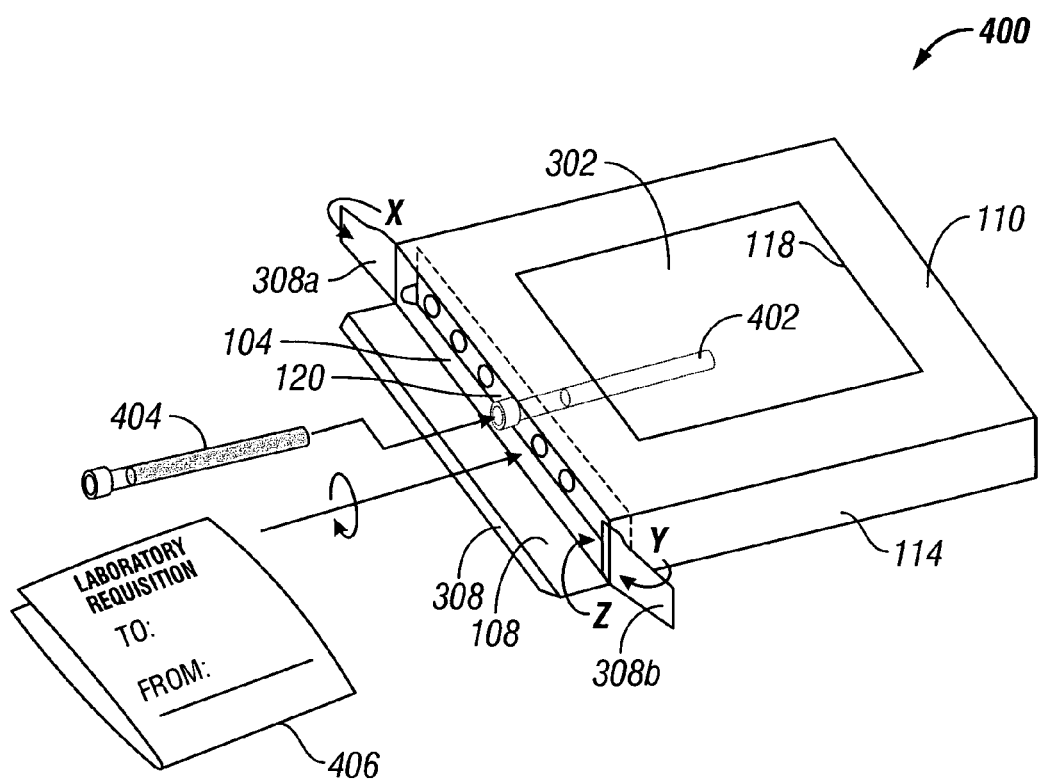
FIG. 7 illustrates a perspective view, shown with bottom-side up, of the system for packaging, having a top end that is open and unclosed and a bottom end that is closed, and containing a specimen vial located in a vial tray of the system, together with an exemplary shipping label (e.g., invoice) showing insertion and use, according to certain embodiments of the invention.

Referring to FIG. 7, the container 400 of FIGS. 4, 5 and 6 (and also the container 100 of FIG. 1) is shown with the bottom end of the container 400 closed. In closing the ends of the container 400, each end is closed by first folding inward the end flaps 108a,b (as shown by arrows X and Y). Then, the top end 108, together with the top lip 308, is folded inward (as shown by arrow Z). The top lip 308 lodges in the container 400, internally adjacent the bottom side 110 at the opening. This forms the enclosure of the container 400. As notable, even when the container 400 is fully closed, as described, a specimen, such as a vial 402, or other contents of the container 400 are viewable through the bottom window 116. Likewise, any paper or other matter contained within the container 400 between the top side 104 and slip ledge 302 (within the container 400), is viewable through the top window 116 of the top side 104 (not shown in FIG. 7, but shown in FIG. 1).

In operation, a bottom end of the container is closed, and a top end of the container is open, to allow for insertion of a specimen, such as a vial 404 (or other matter), and a paper, such as a shipping label 406 (or emblem, identifier, bar code, or other matter). The specimen, such as the vial 404, is inserted into the container 400, through a hole 120a of the vial tray 120. The vial 404 extends through the container 400, between the bottom side 110 and the slip ledge 302, and into viewing range via the bottom window 118. Similarly, a paper, such as the shipping label 406, is inserted into the container 400, through a space between the top side 104 and the slip ledge 302, and into viewing range via the top window 116 (not shown in FIG. 7, but shown in FIG. 1). The shipping label 406 (or other paper, as the case may be) must be oriented with readable information directed into the top window 116 in order for the label 406 to be viewable through the top window 116.

The container 400, and its use in these and other manners, provides packaging that permits viewing of contents, including such matters as specimens and listed information. The container is particularly useful where two separate features or elements contained therein are viewable. For example, in a lab environment, involving packaging for shipping, a specimen can be fitted within the tray structure and maintained thereat, and a documentation can be slipped into the space adjacent the top. In this manner, both the specimen and the documentation can be viewed, for quality control or accuracy or otherwise, through the respective bottom and top windows of the container. Another example for use of the container 400 is for clinical collection kits. In such use, samples (including any applicable bar coding, legends, identifiers, or the like) and relevant documentation (including shipping directions, mail labels, emblems, billing information, forms or the like) can be packed in the container 400. In every event, the windows permit viewing of the contents as desired for the particular application and use. For example, the viewing can allow or enable quality control of the contents of the container 400 after it is sealed.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems and any element(s) that may cause any benefit, advantage, or solution to occur or become more pronounced are not to be construed as a critical, required, or essential feature or element of any or all the claims. As used herein, the terms "comprises, "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A collection package for a lab specimen, comprising:
  a top;
  a first side, connected to the top;
  a bottom, connected to the first side;
  a second side, connected to the bottom; and
  an internal separator having a retainer formed therein for holding the specimen in position relative to the internal separator;
  wherein the internal separator forms a first compartment and a second compartment, further comprising:
  a window for viewing the first compartment; and
  a second window for viewing the second compartment;
  wherein the top, the first side, the bottom, the second side, and the internal separator are all formed by folding of a planar sheet.

2. A method of forming a container for a content, comprising the steps of:
  folding a sheet to form a first side;
  folding the sheet to form a top;
  folding the sheet to form a second side;
  folding the sheet to form a bottom;
  folding the sheet to form an internal separator;
  forming a retainer hole in the internal separator, suitable for retaining the content of the container;
  forming a first window in the top; and
  forming a second window in the bottom.

* * * * *